United States Patent
Roloff et al.

(10) Patent No.: US 7,879,378 B2
(45) Date of Patent: Feb. 1, 2011

(54) PROCESS FOR THE SEPARATION AND SENSORY EVALUATION OF FLAVOURS USING HTLC

(75) Inventors: Michael Roloff, Oberweser (DE); Harry Erfurt, Uslar (DE); Günter Kindel, Höxter (DE); Claus-Oliver Schmidt, Holzminden (DE); Gerhard E Krammer, Holzminden (DE)

(73) Assignee: Symrise GmbH & Co. KG, Holzminden (DE)

( * ) Notice: Subject to any disclaimer, the term of this patent is extended or adjusted under 35 U.S.C. 154(b) by 538 days.

(21) Appl. No.: 11/911,983

(22) PCT Filed: Apr. 6, 2006

(86) PCT No.: PCT/EP2006/061362

§ 371 (c)(1), (2), (4) Date: Jun. 5, 2008

(87) PCT Pub. No.: WO2006/111476

PCT Pub. Date: Oct. 26, 2006

(65) Prior Publication Data

US 2008/0268118 A1    Oct. 30, 2008

Related U.S. Application Data

(60) Provisional application No. 60/673,592, filed on Apr. 21, 2005.

(51) Int. Cl.
*G01N 30/88* (2006.01)
(52) U.S. Cl. .................... 426/424; 426/474
(58) Field of Classification Search ............. 426/424, 426/474
See application file for complete search history.

(56) References Cited

U.S. PATENT DOCUMENTS

| 5,345,029 | A | 9/1994 | Schubert et al. | |
| 2009/0272204 | A1* | 11/2009 | Roloff et al. | 73/865.7 |
| 2009/0274812 | A1* | 11/2009 | Roloff et al. | 426/474 |

FOREIGN PATENT DOCUMENTS

| EP | 0878711 | 11/1998 |
| FR | 2856796 | 12/2004 |
| WO | 0222075 | 3/2002 |

* cited by examiner

*Primary Examiner*—Anthony Weier
(74) *Attorney, Agent, or Firm*—Roylance, Abrams, Berdo & Goodman, L.L.P.

(57) ABSTRACT

The present invention concerns a process for the separation of olfactorily and/or gustatorily active components by means of high-temperature liquid chromatography (HTLC) and a process for the direct tasting of the components separated by this process.

8 Claims, 1 Drawing Sheet

PROCESS FOR THE SEPARATION AND SENSORY EVALUATION OF FLAVOURS USING HTLC

FIELD OF THE INVENTION

Figure 1:
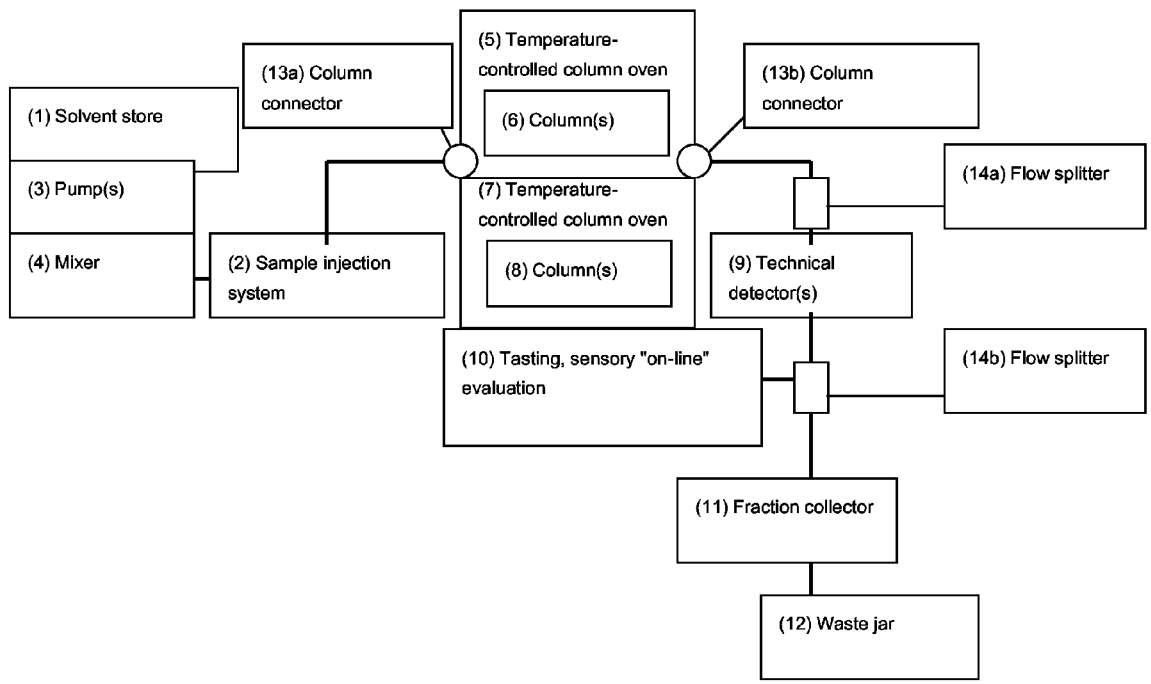

The present invention concerns a process for the separation of olfactorily and/or gustatorily active components by means of high-temperature liquid chromatography (HTLC) and a process for the direct tasting of the fractions obtained by this process.

BACKGROUND OF THE INVENTION

Flavour compositions (commonly also known as flavours) contain at least two different sensorially active substances such as, for example, synthetic, natural or nature-identical aromatic substances or plant extracts. Mostly, however, flavours are complex mixtures of many sensorially active components. The sensorially active substances can be volatile (odorous or aromatic substances) or non-volatile (flavouring substances). Volatile aromatic substances can be perceived by human beings both orthonasally and retronasally. Flavouring substances interact with the flavour receptors on the tongue and are responsible for the gustatory (taste) impressions sweet, sour, bitter, salty and umami; in addition, other, often trigeminal stimuli, such as e.g. pungent, burning, cooling, tingling or prickling effects, are also perceived. The proportions of the sensorially active substances in a flavour composition can vary enormously and they naturally have a strong influence on the overall sensory impression of the flavour composition. It is not the absolute amount of a sensorially active component in a flavour which is decisive, but its sensory contribution. Many sensorially important components in foodstuffs are not even known yet, since they are contained in only very small amounts, even though because of their high sensory activity they make a significant olfactory and/or gustatory contribution. More meaningful than the simple amount is therefore the so-called odour activity value, which is defined as the quotient of the concentration of a sensorially active component and its olfactory or gustatory threshold value.

It is often desirable to determine the sensorially active constituents of a flavour composition and to this end to fractionate the flavour composition in order to develop new gustatorily attractive flavour compositions and also for quality control purposes in the production of flavour compositions. The sensory evaluation of the individual fractions is conventionally carried out by means of dilution analysis. An overview of this topic can be found in Chemie in unserer Zeit 2003, 37, 388-401 and in the literature cited therein.

A conventional fractionation process is high-performance liquid chromatography (HPLC). A further development of HPLC is high-temperature liquid chromatography (HTLC), in which temperature-programmable HPLC ovens and temperature-stable HPLC columns are used. The person skilled in the art can find an overview of HTLC in the publication LABO (Magazin für Labortechnik & Life Sciences), March 2004 edition, 19-22.

In GC/olfactometry, a mixture of odorous, volatile components is separated by gas chromatography and the olfactorily relevant components are inhaled through the nose at a gas outlet from the gas chromatograph in carrier gas and ambient air and are olfactorily evaluated; the perception is thus exclusively orthonasal. An overview of this can be found for example in the monograph "ACS Symposium Series 782, Gas Chromatography—Olfactometry", Oxford University Press, 2001.

In JP 09-248164 (Hitachi Zosen Corp.) the flavour of tea extracts is determined by means of HPLC analysis. The ratios of the peak areas of certain sensorially active components serve as a quality standard for the flavour of the tea. A mixture consisting of water, 13% methanol and 0.1% phosphoric acid was used as the mobile phase for the HPLC method performed therein. The process conditions for the HPLC separation, the way in which the eluted fractions are freed from methanol and the procedure for sensory evaluation are not described in any further detail.

In customary HPLC separating processes for the analysis of flavour compositions, mobile phases (eluents) are conventionally used which are miscible with water but which are organic and harmful or toxic solvents. Commonly used eluents are acetonitrile, methanol and tetrahydrofuran as well as mixtures thereof with water or aqueous buffers. The harmful solvents must be removed from an eluted fraction before a sensory evaluation. This removal requires the use of time-consuming, mostly thermal or extractive processes such as distillation or freeze-drying, for example. These processes often result in a change in the composition of the flavouring and aromatic substances contained in the eluted fraction, due in particular to thermal and/or oxidative influences. Accordingly, the sensory properties of the eluted fractions of a flavour composition frequently differ considerably from those of the original composition. Following removal of the harmful solvents, the eluted and isolated sensorially active components must be taken up in a harmless solvent and sensorially evaluated by means of dilution analysis. The dilution analysis and the subsequent sensory evaluation are not automated processes. Until now only time-delayed ("off-line") and relatively complex processes for the separation and tasting of flavour compositions have been described in the prior art.

SUMMARY OF THE INVENTION

A further disadvantage is that sensorially active components which are unable to be recorded with technical detectors cannot be detected by conventional separating processes, for example because of their low concentration in the flavour composition to be separated and/or due to a lack of the structural properties necessary for technical detection.

DETAILED DESCRIPTION OF THE INVENTION

Also known are processes wherein an evaluation is made by electronic sensor systems ("in vitro") instead of by tasting by a person. However, this evaluation is commonly not transferable or not adequately transferable to the taste impression of a person.

An immediate or synchronous sensory evaluation of the separated components during the separation process, in an analogous manner to orthonasal evaluation in GC/olfactometry, is not possible with the hitherto known processes.

The object of the present invention was to provide a process for an immediate ("on-line") or synchronous sensory taste and aroma evaluation of flavour compositions by people ("in vivo"). The process should also allow the analysis of as many different flavour compositions as possible.

According to one aspect the present invention thus concerns a process for the separation of a flavour composition by means of high-temperature liquid chromatography (HTLC)

with a stationary phase and an eluent (mobile phase), and is characterised in that a chromatography step is performed wherein (a) the temperature of the stationary phase is in the range of from 100 to 400° C.,
(b) the pressure is in the range of from 30 to 250 bar, and
(c) the eluent used is harmless and has a water content of at least 25 wt. %, based on the overall weight of the eluent.

The flavour composition to be separated preferably contains at least one volatile aromatic substance. Within the context of the present invention, a volatile aromatic substance is understood to be preferably a sensorially active component having a vapour pressure of greater than or equal to 0.01 Pa at 25° C., in particular having a vapour pressure of greater than or equal to 0.025 Pa at 25° C. A majority of volatile aromatic substances has a vapour pressure of greater than or equal to 1 Pa at 25° C., such that in particular such substances are regarded as volatile aromatic substances within the meaning of the present invention.

It has now been found that a time-synchronous tasting is possible through a targeted choice of HTLC conditions using harmless eluents. The tasting is an "in vivo" sensory evaluation by people, wherein the material to be tasted is taken in the mouth and optionally swallowed. Harmless substances (particularly eluents) are in particular the solutions, solvents and diluents classed as harmless according to pharmaceutical standards. Harmless eluents can be swallowed by a person. They are understood to be eluents which do not have the hazard symbol T+ (very toxic substances), T (toxic substances) or Xn (harmful substances). Furthermore, preferred harmless eluents do not have the hazard symbol Xi (irritant substances).

Preferred harmless eluents have none of the hazard indications (so-called "R phrases") from the group R14, R15, R20, R21, R22, R23, R24, R25, R26, R27, R28, R29, R36, R37, R38, R39 and R40 or correspondingly combined R phrases (such as e.g. R23/24/25).

Surprisingly it has now been found that a good separation of many different flavour compositions into individual fractions is possible even using harmless eluents, such that the conventionally indispensable use of harmful or even toxic eluents can be eliminated. The process according to the invention thus firstly allows, immediately following a chromatographic separation of a flavour composition, in other words shortly after or even synchronously to the separation, a tasting of the sensorially active components of a flavour composition by a person. In particular, the process according to the invention allows an ortho- and retronasal and lingual and trigeminal sensory evaluation of the fractions obtained to be performed simultaneously.

In particularly preferred processes according to the invention the temperature during the chromatography step is in the range of from 100 to 200° C.

Alternatively or in addition, the pressure during the chromatography step is in the range of from 50 to 200 bar. Alternatively or in addition to each of the aforementioned variants of the process according to the invention, the water content of the eluent is preferably at least 40 wt. %, particularly preferably at least 50 wt. %, particularly preferably 60 to 100 wt. %, based in each case on the overall weight of the eluent.

An important aspect of the present invention is presumably that under the conditions according to the invention during the HTLC process the water in the eluent is in the superheated state (superheated water). Superheated, or in the extreme case supercritical, water exhibits different solvent properties than under conventional HPLC conditions (for example the density and/or polarity of the water change), which surprisingly are particularly suitable for the separation of flavour compositions.

The eluent is preferably pumped through the stationary phase at a flow rate of 0.1 to 30 ml/min, preferably at a flow rate of 0.2 to 20 ml/min.

The ranges for temperature of the stationary phase, flow rate of the eluent and pressure used in the process according to the invention also depend on the particle size of the column material used in the separating column, so that in an individual case the ranges given for these parameters can vary somewhat.

In addition to pure water, aqueous mixtures having an aforementioned preferred water content are particularly advantageous as eluents, these aqueous mixtures preferably containing one or more constituents selected from the group consisting of ethanol, propylene glycol, glycerol, triacetin (glycerol triacetate), physiologically compatible salts (for example sodium chloride), physiologically compatible acids (for example phosphoric acid, acetic acid), physiologically compatible buffer substances (for example sodium phosphates, sodium acetate), oils and fats, the concentration of the constituent(s) in the eluent conveniently being chosen in each case such that the eluent as a whole remains harmless. These eluents used according to the invention can be in the form of solutions or emulsions.

According to the invention, eluents in the form of aqueous solutions are preferred which contain one or more constituents chosen from the group consisting of ethanol, propylene glycol, glycerol, physiologically compatible salts (e.g. sodium chloride), physiologically compatible acids (e.g. phosphoric acid, acetic acid) and/or physiologically compatible buffer substances (e.g. sodium phosphates, sodium acetate), particularly preferred eluents are aqueous solutions containing ethanol and/or propylene glycol.

Particularly preferred eluents are those which consist substantially (i.e. at least 95 wt. %, preferably at least 98 wt. %) or entirely of water and ethanol, the ethanol content in turn being preferably in the range from 1 to 50 wt. %, particularly preferably in the range from 5 to 30 wt. %. The specified percentages by weight are based in each case on the overall weight of the eluent. Too high a proportion of ethanol can adversely affect the sensory evaluation of the sensorially active components during tasting. In order to increase the sensory detection sensitivity, the proportion of eluent can be increased by atomising the eluate in a gas stream (preferably air or nitrogen) and optionally evaporating the atomised eluate in a heater. In addition, a reduction of disruptive, high ethanol proportions can take place, before tasting, by membrane separation or by adsorption methods. In the case of the particularly preferred eluents, which consist substantially or entirely of water and ethanol, in particular those consisting of 5 to 30 wt. % ethanol and 95 to 70 wt. % water, the temperature of the stationary phase is preferably in the range of from 100 to 150° C. and the pressure is preferably in the range of from 30 to 150 bar, more preferably in the range of from 30 to 100 bar.

If the eluent contains physiologically compatible salts (for example sodium chloride), physiologically compatible acids (for example phosphoric acid, acetic acid) and/or physiologically compatible buffer substances (for example sodium phosphates, sodium acetate), the overall proportion of these salts, acids and/or buffer substances is preferably less than or equal to 10 wt. %, preferably less than or equal to 5 wt. %, particularly preferably in the range from 0.001 to 2 wt. %, based in each case on the overall weight of the eluent.

Depending on the separating problem, it can be advantageous to chromatograph with an elution gradient. For instance, at the start of elution the mobile phase can consist of pure water and be gradually changed into a mixture of ethanol and water by increasing the ethanol content in the mobile phase as the elution time increases.

An immediate tasting of the components purified according to the invention is of great advantage, since not only does an orthonasal perception occur, as is the case in GC/olfactometry, but lingual, retronasal and trigeminal stimuli can be perceived at the same time. In addition, a tasting of freely selectable fractions is possible, such that aromatic and flavouring substances can be tasted in differing concentrations. In particular, the process according to the invention allows a gustatory evaluation to be performed during the course of the elution almost "anywhere along the HTLC peak", in other words at freely selectable times during the elution. In this way an evaluation can be made of the sensorially active component in varying concentrations or dilutions during the elution. The process according to the invention also offers the possibility of optimising the sensory analysis, for example for authenticity testing of natural mixtures containing complex flavours or aromatic substances. Thus mixtures of substances can be separated reproducibly with the process according to the invention and tasted in parallel with the separation. This permits a substantially more accurate sensory quality analysis and a very precise sensory comparison with reference samples. The process according to the invention can thus be used for example for the authenticity analysis of spices, spice extracts, essences or other mixtures containing natural products, such as ground pastes for example (e.g. chocolate hazelnut spread).

The components separated by chromatography with the harmless eluents are preferably also fed to a technical detector system and after leaving the detector or on leaving a sample splitter, for direct sensory evaluation, are passed to the mouth and tasted. To optimise the sensory evaluation, a reference (mixture) can be used, preferably consisting of the eluent or, if the eluent is a mixture, the individual components of the eluent.

Surprisingly it has been found that the "on-line" tasting with the aid of the process according to the invention including its preferred variants allows a time-synchronous evaluation with adequate sensitivity for many important aromatic substances (particularly vanillin, maltol, furaneol) and flavouring substances (particularly caffeine, sucrose). On the basis of the prior art it would have been expected that the time needed for the separation would not correlate with the time needed for the gustatory evaluation. It would moreover have been expected that the dilution by the eluent would lead to a lower sensitivity.

In a further aspect the present invention concerns a process for the sensory evaluation of a separated flavour composition, characterised by the following steps:
1. Performance of an HTLC process according to the invention to obtain an eluate fraction,
2. Cooling of the eluate fraction to a temperature of less than or equal to 50° C., and then
3. Sensory evaluation of this cooled eluate fraction immediately following the performance of step 2 by tasting by a person.

The sensory evaluation and tasting can also include the detection of physiologically active compounds which in contact with the mucous membranes of the mouth and pharynx provoke physiological effects such as burning, scratching, cooling, heating, numbness and/or narcotic sensations.

Cooling of the eluate fraction can naturally also be carried out to temperatures of less than or equal to 30° C., such as e.g. room temperature (around 20° C.), and is primarily determined by the desired tasting conditions.

The HTLC process according to the invention and the subsequent tasting can be standardised and largely automated, such that mutually comparable test results can be obtained for the separated flavour compositions.

Through the sensory "on-line" evaluation, the process according to the invention allows in particular a direct sensory identification and evaluation of volatile and non-volatile components (individual substances and mixtures of substances) of a flavour composition, and a selective fractionation of the eluate obtained by the HTLC process according to the invention by means of the sensory "on-line" evaluation of the eluate. For the first time, the use of the process according to the invention allows the evaluation of sensorially active components to be performed quickly and at low cost and the substances in the test material that are relevant for organoleptic reception by a person to be determined.

All materials which are conventionally taken in the mouth by a person are suitable as the test material. These are, for example, food ingredients, foodstuffs, such as drinks, yoghurts, desserts, ice creams, soups, sauces, bread spreads, spicy snacks, meat, fish, fruit, vegetables, nuts, ready meals (such as pizza, gourmet salads and baby foods), sweets (such as chocolate, toffees, fruit gums) and chewing gum, oral care products, such as toothpastes and mouthwashes, animal food, such as moist and dry food, and medicaments, such as cough syrup, lozenges and chewing tablets. Extracts obtained from the test materials by means of chewing apparatus (see e.g. U.S. Pat. No. 6,547,172 B2) or dissolution testers are also suitable for performing the process according to the invention. In this way the behaviour of sensorially active components can be studied in and out of different matrices. Using the data obtained, the behaviour of the components in the matrices can then be selectively influenced.

The process according to the invention and a device which is particularly suitable for performing the process is described below by reference to the embodiment examples and FIG. 1, without the scope of protection with regard to the claims being limited by this.

EXAMPLE 1

Device for Performing a Process According to the Invention

FIG. 1 shows a device for performing the process according to the invention. The device includes two HTLC columns (6, 8), wherein each of the columns is positioned in its own temperature-controlled oven (5, 7). At one sample injection end the columns (6, 8) are each connected via a column connector (13a), in particular a multidirectional valve, to a sample injection system (2), for example an autosampler. At one sample injection end the columns (6, 8) are each connected via a further column connector (13b), in particular a multidirectional valve, to one or more technical detectors (9), for example a refractive index detector (RI), an evaporative light-scattering detector (ELSD), a mass spectrometer detector (MS), a diode-array detector (DAD), a UV/Vis detector and/or a fluorescence detector (FLD). In the direction of flow before (14a) and/or after (14b) the technical detector(s) (9) there is a flow splitter to release a split stream of eluate for tasting (10) by a person. A fraction collector collects the untasted split streams of eluent and feeds them to a waste jar (12).

The device depicted in FIG. 1 includes two different HTLC column types (6, 8) for different analytical emphases. The ovens (5, 7) allow the temperature of the columns (6, 8) to be controlled separately and the column connector (13a) enables elution to be performed with different eluents and in particular with eluent gradients. The device for use according to the invention can also include just one temperature-stable chromatographic column; the simultaneous use of two or more (up to six depending on the configuration) temperature-stable chromatographic columns is often convenient.

EXAMPLE 2

Testing of an Instant Cappuccino Product Using the Process According to the Invention Preparation of a sample solution in water in a defined concentration.

The HTLC device for use according to the invention contains two column ovens (5, 7), each with a separating column (6, 8), wherein the first separating column (6) contains a polymer phase for the carbohydrate analysis and the second separating column (8) contains a polymer phase for the bitter principle analysis. The dimensions of the column used for the carbohydrate analysis are 250×8 mm and those of the column for the bitter principle analysis are 250×8 mm. A combined detector comprising an RI, ELSD and DAD is used as the technical detector (9).

The device according to the invention is conditioned with a flow of 1.5 ml/min of an eluent comprising 100% water.

The sample injection system (2) in the device is set to a sample injection quantity of 50 µl.

On completion of the conditioning step, chromatographic analysis is performed according to the programme below:

| Time [min] | 3 [ml/min] | 3a [%] | 3b [%] | 7 [° C.] | 5 [° C.] | 9a RI | 9b ELSD | 9c DAD |
|---|---|---|---|---|---|---|---|---|
| 0 | 1.5 | 100 | 0 | 40 | 80 | on | on | on |
| 60 | 1.5 | 100 | 0 | 40 | 80 | on | on | on |
| 80 | 1.5 | 100 | 0 | 40 | 80 | on | on | on |
| 81 | 0 | 100 | 0 | 40 | off | off | on | on |
| 82 | 1.5 | 100 | 0 | 40 | off | off | on | on |
| 100 | 1.5 | 100 | 0 | 150 | off | off | on | on |
| 110 | 1.5 | 50 | 50 | 150 | off | off | on | on |
| 115 | 3 | 50 | 50 | 150 | off | off | on | on |
| 120 | 3 | 50 | 50 | 150 | off | off | on | on |

The changes in temperature, flow rate and eluent composition during the program take place in a linear manner.

As soon as one of the three detectors displays a signal (peak), the sensory evaluation of the eluate fraction (split stream) emerging from the flow splitter (14*b*) is performed as soon as it is cooled to a temperature of 50° C. or less. A sensory evaluation time-synchronised to the measured peak ("on-line") thus takes place. The sensory evaluation by tasting can be performed by one or more testers; the flavour impression of the tasted fraction is documented at the appropriate detector signal.

EXAMPLE 3

Testing of a Chocolate Extract Using the Process According to the Invention

An ethanolic extract of a chocolate is prepared and separated using an HTLC device for use according to the invention.

The HTLC device for use according to the invention contains a column oven (5) with a separating column (6). A polymer phase [Hamilton PRP-1 reversed phase HPLC column, spherical styrene-divinyl benzene copolymer, particle size: 10 µm, pore size 100 Å, dimensions (length×internal diameter): 250×10 mm] was used as the separating column. A combined detector comprising an RI, ELSD and DAD is used as the technical detector (9).

Elution was performed at a flow rate of 1 to 3 ml/min with an elution gradient, wherein a mixture comprising 95 wt. % water and 5 wt. % ethanol was used as eluent at the start and a mixture comprising 70 wt. % water and 30 wt. % ethanol at the end of the HTLC separation. The temperature of the stationary phase was raised continuously during the HTLC separating process from 100° C. at the start to 150° C. at the end, the pressure being decreased from 100 bar at the start to 30 bar at the end.

The sensorially active substances maltol, vanillin (vapour pressure: 0.0272 Pa at 24.1° C.), theobromine and caffeine were separated in this way and were individually sensorially tasted.

The invention claimed is:

1. A method for separating a flavour composition with a high-temperature liquid chromatography (HTLC) having a stationary phase and an eluent (mobile phase), wherein a chromatography step is performed, with:
   (a) a temperature of the stationary phase in a range of 100 to 400° C.,
   (b) a pressure in a range of 30 to 250 bar, and
   (c) a eluent being harmless and having a water content of at least 25 wt. %, based on the overall weight of the eluent.

2. The method according to claim 1, wherein the temperature of the stationary phase is preferably in the range of 100 to 200° C.

3. The method according to claim 1, wherein the pressure is preferably in the range of 50 to 200 bar.

4. The method according to claim 1, wherein the eluent preferably has a water content of at least 40 wt. %, based on the overall weight of the eluent.

5. The method according to claim 1, wherein the eluent includes at least one of ethanol, propylene glycol, glycerol, triacetin, physiologically compatible salts, physiologically compatible acids, physiologically compatible buffer substances, oils or fats.

6. The method according to claim 1, wherein the eluent consists substantially of water and ethanol.

7. The method according to claim 1, wherein the eluent includes ethanol in a proportion of 1 to 50 wt. %, based on the overall weight of the eluent.

8. A method for the sensory evaluation of a separated flavour composition, comprising by the following steps of:
   1. Performing an HTLC process to obtain an eluate fraction,
   2. Cooling the eluate fraction to a temperature of less than or equal to 50° C., and
   3. Evaluating the cooled eluate fraction by tasting by a person immediately following said step of cooling the eluate fraction to a temperature of less than or equal to 50° C.

* * * * *

UNITED STATES PATENT AND TRADEMARK OFFICE
CERTIFICATE OF CORRECTION

| | | |
|---|---|---|
| PATENT NO. | : 7,879,378 B2 | Page 1 of 1 |
| APPLICATION NO. | : 11/911983 | |
| DATED | : February 1, 2011 | |
| INVENTOR(S) | : Michael Roloff et al. | |

It is certified that error appears in the above-identified patent and that said Letters Patent is hereby corrected as shown below:

Claim 8 (column 8, line 50), delete "following".

Signed and Sealed this
Twenty-second Day of March, 2011

David J. Kappos
*Director of the United States Patent and Trademark Office*